(12) United States Patent
Yao

(10) Patent No.: US 6,517,511 B2
(45) Date of Patent: Feb. 11, 2003

(54) CLEANSABLE MULTI-PURPOSE NASAL DISCHARGE ASPIRATOR

(76) Inventor: Tzu-Chiang Yao, 10F-8, No. 18, Lane 609, Sec. 5, Chung Hsin Rd., San Chung City, Taipei Hsien (TW)

( * ) Notice: Subject to any disclaimer, the term of this patent is extended or adjusted under 35 U.S.C. 154(b) by 11 days.

(21) Appl. No.: 09/886,017

(22) Filed: Jun. 22, 2001

(65) Prior Publication Data

US 2002/0198488 A1 Dec. 26, 2002

(51) Int. Cl.[7] .................. A61M 1/00; A61M 1/06; A61F 11/00
(52) U.S. Cl. .................. 604/35; 604/73; 604/319; 604/315; 606/162
(58) Field of Search .................. 604/35, 73, 313–315, 604/319; 606/162

(56) References Cited

U.S. PATENT DOCUMENTS

| | | | | |
|---|---|---|---|---|
| 1,882,040 A | * | 10/1932 | Roehm | |
| 3,906,940 A | * | 9/1975 | Kawada | |
| 4,776,840 A | * | 10/1988 | Freitas et al. | |
| 4,982,739 A | * | 1/1991 | Hemstreet et al. | |
| 4,998,915 A | * | 3/1991 | Hannah | |
| 5,295,956 A | * | 3/1994 | Bales et al. | |
| 5,395,312 A | * | 3/1995 | Desai | |
| 5,718,668 A | * | 2/1998 | Arnett et al. | |
| 6,019,749 A | * | 2/2000 | Fields et al. | |
| 6,059,803 A | * | 5/2000 | Spilman | |
| 6,135,980 A | * | 10/2000 | Vu | |
| 6,149,622 A | * | 11/2000 | Marie | |

* cited by examiner

Primary Examiner—Dennis Ruhl

(57) ABSTRACT

A cleansable multi-purpose nasal discharge aspirator is easily cleanable by constructing its housing hermetical and water tight so that the aspirator is submergible for washing its inner pressure chamber. Its multi-purpose effect is carried out by replacing its sucking disc into variety of tool heads so as to perform various missions such as imbibing acnes other than its principal application, inhaling nasal discharge. Besides, this aspirator is able to serve as an eyes or nose syringing apparatus by replacing its sucking disc into a special tool head and adding a water intake tube and a water ejection tube.

4 Claims, 4 Drawing Sheets

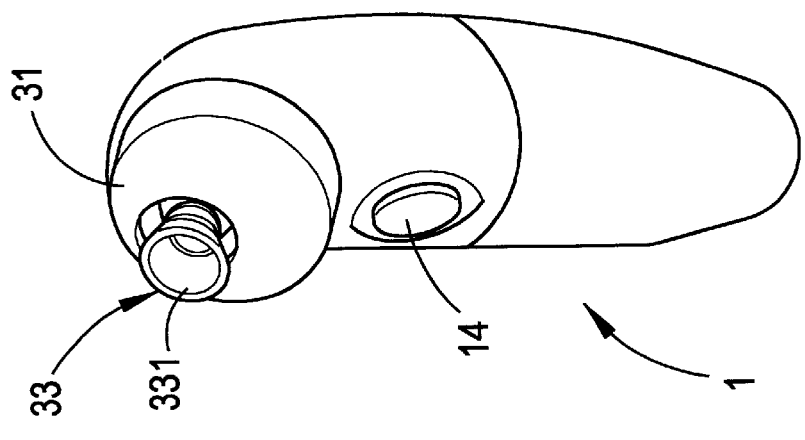
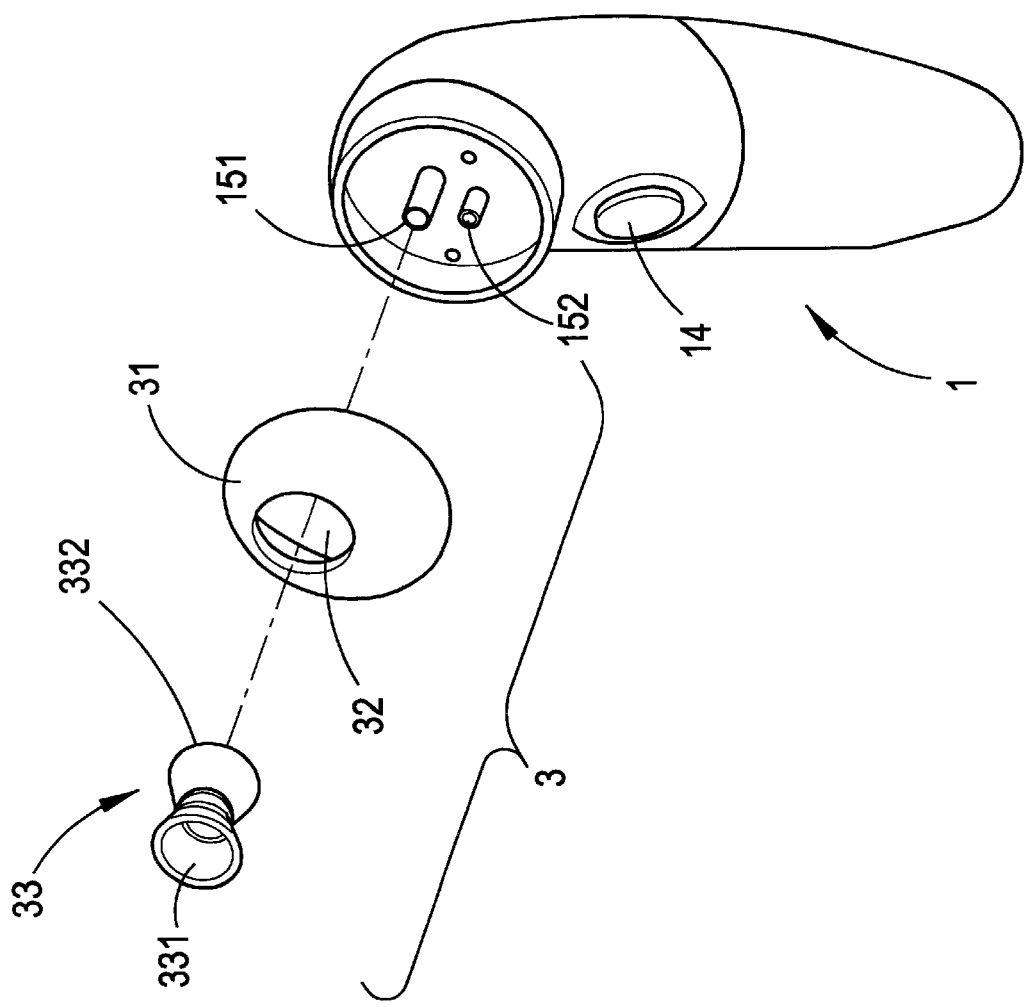

CLEANSABLE MULTI-PURPOSE NASAL DISCHARGE ASPIRATOR

BACKGROUND OF THE INVENTION

1. Field of the Invention

The present invention relates to a nasal discharge aspirator, in particular, the nasal discharge aspirator is easily cleansable, and replaceable with variety of tool heads so as to attain multi-purpose usage in constantly wholesome state.

2. Description of the Prior Art

A nasal discharge aspirator is an apparatus for inhaling nasal discharge from a patient's nares. It is essentially composed of a pressure chamber and a nasal discharge aspirating tube. By means of the air pressure produced from the pressure chamber the patient's nasal discharge is drawn into the aspirator and collected therein.

As the function of aforesaid nasal discharge aspirator is so simple that its basic structure has not been improved or changed for a long time.

As a matter of fact, there are several shortcoming inherent to such a conventional electric motor driven nasal discharge aspirator which needs a further improvement. As the nasal discharge container, pressure pump (in a chamber), and a battery unit is concentrated in one space without proper isolation therebetween, the inhaled nasal discharge is apt to flow here and there and stick to pressure pump causing pollution or clogging, microorganisms and parasites remaining therein can not be thoroughly by ordinary cleansing process.

Furthermore, there are analogous aspirators on the market, for example, nasal discharge aspirator, acne imbiber (acne vacuum massager), nose or eye syringe etc. They are commonly characterized in that the work is accomplished by a force produced from sucking and discharging a pressurized fluid through a conducting tube, but each one carries out its own single function and is not able to serve in multi-purposed way.

Inherent problem of difficult to clean up the apparatus as that described above remains all the same because if a strong water jet stream is employed to cleanse these aspirators, the electrical insulation for the driving motor will definitely punctures.

In view of the foregoing situation, the inventor of the present invention herein conducted intensive research based on many years of experience gained through professional engagement in the manufacturing of related products, with continuous experimentation and improvement culminating in the development of the improved structure for cleansable multi-purpose nasal discharge aspirator of the present invention herein.

SUMMARY OF THE INVENTION

It is an object of the present invention to provide cleansable multi-purpose nasal discharge aspirator which is equipped with a sucking disc having a nasal discharge barrier unit so as to gather the nasal discharge in a restricted region therein thereby protecting the pressure chamber and mechanical part of the aspirator from being contaminated. The sucking disc is detachable from the aspirator housing so as to easily discard the dirty content thereby keeping the apparatus always in a clean state.

It is another object of the present invention that the above provided aspirator is enclosed with a water tight housing able to withstand submerging in water for cleaning, while the gas chamber inside is also hermetically constructed so as to keep out infringement of inhaled air or water into the mechanical parts such as the driving motor and the pressure pump, and the inner part of the aspirator is cleansable with a water jet stream.

It is a further object of the present invention that the above provided aspirator is functionable for sucking and ejecting all kinds of fluidal flow, accordingly, variety of working heads is attachable to this aspirator for performing multi-purpose effect, for example to imbibe acnes with a pressurized air flow, and syringing eyes or nose with a water jet flow such that one of this apparatus of the present invention can cope with a plurality of conventional apparatus of single function thereby greatly cutting down the user's cost.

To achieve these and other objects, the aspirator of the present invention is composed of a housing, a power supply source, a driving motor, a pressure pump, a switch, a pressure chamber, a detachable sucking disc, an inhaling tube, an air conducting tube, and a barrier unit.

The power supply source (battery unit), the driving motor, the pressure pump for producing pressurized fluid, are all accommodated in the housing, and the switch for controlling motor ON/OFF, is mounted on the outer surface of the housing. The pressure chamber provided at the front end of the housing and having an air intake aperture and an air discharge aperture is connected with an open end of the pressure pump. The detachable sucking disc is fitted to the air intake aperture from outer side of the housing, while the air discharge aperture is communicated with the outside of the housing. The inhaling tube is connected to the front end of the sucking disc, and the air conducting tube is connected to the joint portion of the sucking disc and the air intake aperture. The barrier unit is interposed between the inhaling tube and the air conducting tube.

The barrier unit includes a tubular spacer and a plurality of slanted arcuate baffles.

The air conducting tube is encompassed by the tubular sparer, and the slanted arcuate baffles are radially disposed between the tubular spacer and the inner fringe on the base of the sucking disc such that a pressure is produced by actuating the pressure pump and inhales the nasal discharge into the sucking disc through the inhaling tube, the inhaled nasal discharge is detained in the slanted arcuate baffles region by the tubular spacer so as to keep the nasal discharge in a restricted region and not to infringe into the pressure chamber to contaminate the apparatus. The remaining inhaled air is released from the discharge aperture by way of the air conducting tube and the air intake aperture.

The used sucking disc can be detached and sterilized for reuse.

Meanwhile, variety of working heads is replaceable for the sucking disc for carrying out different functions as stated above.

BRIEF DESCRIPTION OF THE DRAWINGS

The drawings disclose several illustrative embodiments of the present invention which serve to exemplify the various advantages and objects hereof, and are as hollows:

FIG. 5 is an exploded cross sectional view in a second embodiment of the present invention;

FIG. 6 is a three dimensional view showing the assembled unit in a second embodiment of the present invention;

DETAILED DESCRIPTION OF THE PREFERRED EMBODIMENT

Figure 1:
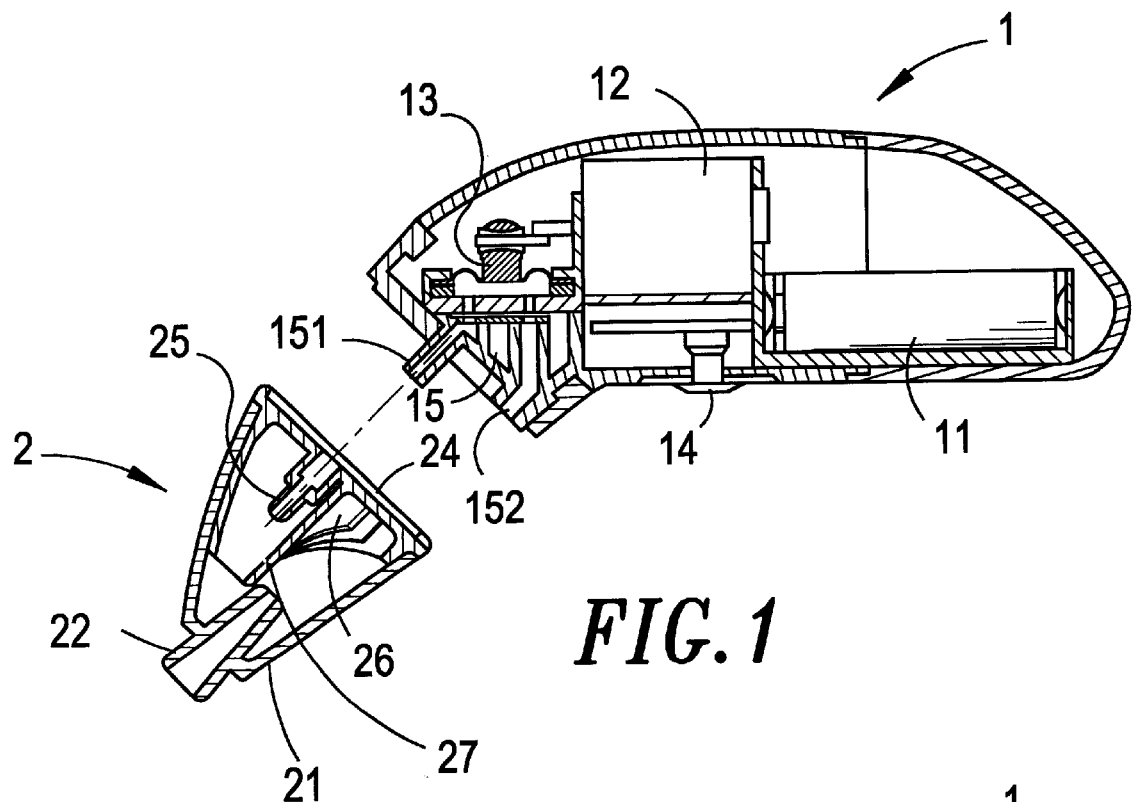
FIG. 1 is an exploded cross sectional view of the present invention.
Figure 2:
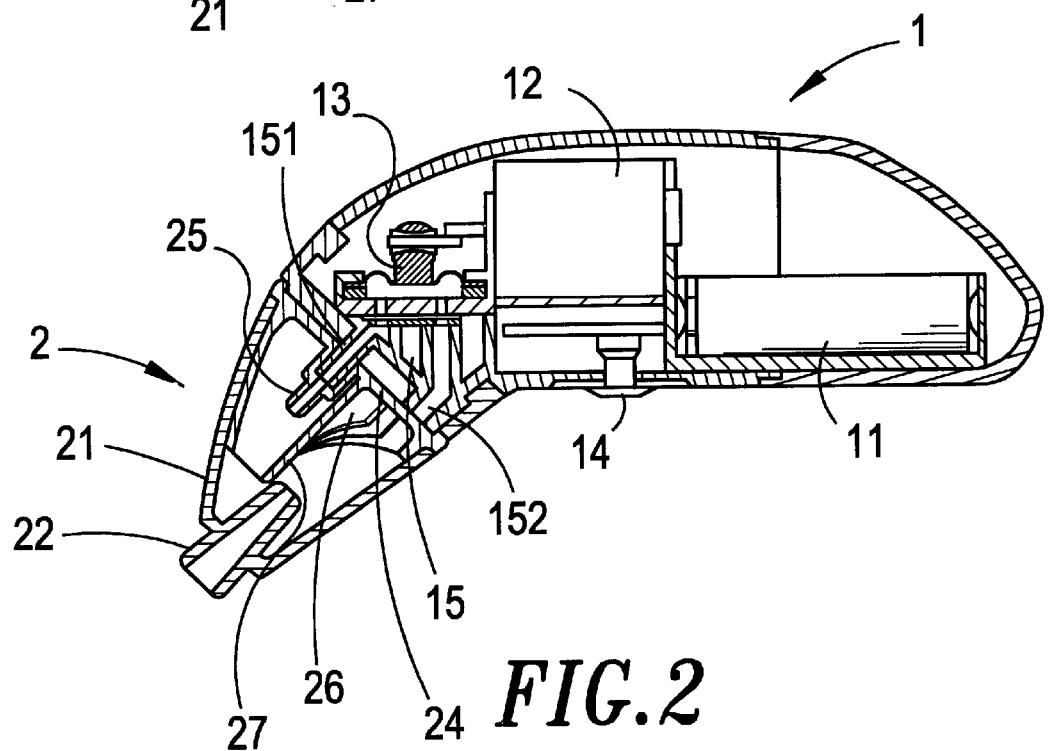
FIG. 2 is a cross sectional view of the assembled unit of the present invention.
Figure 4:
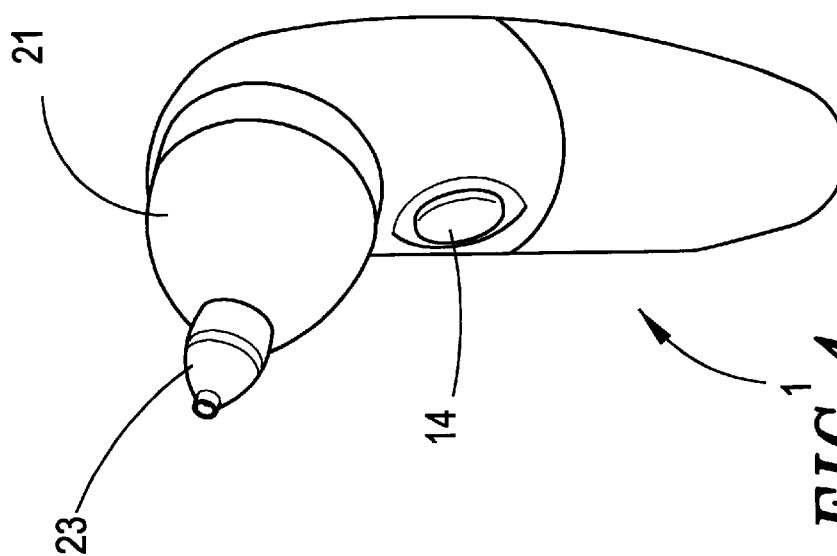
FIG. 4 is a three dimensional view showing the assembled unit of the present invention.
Figure 3:
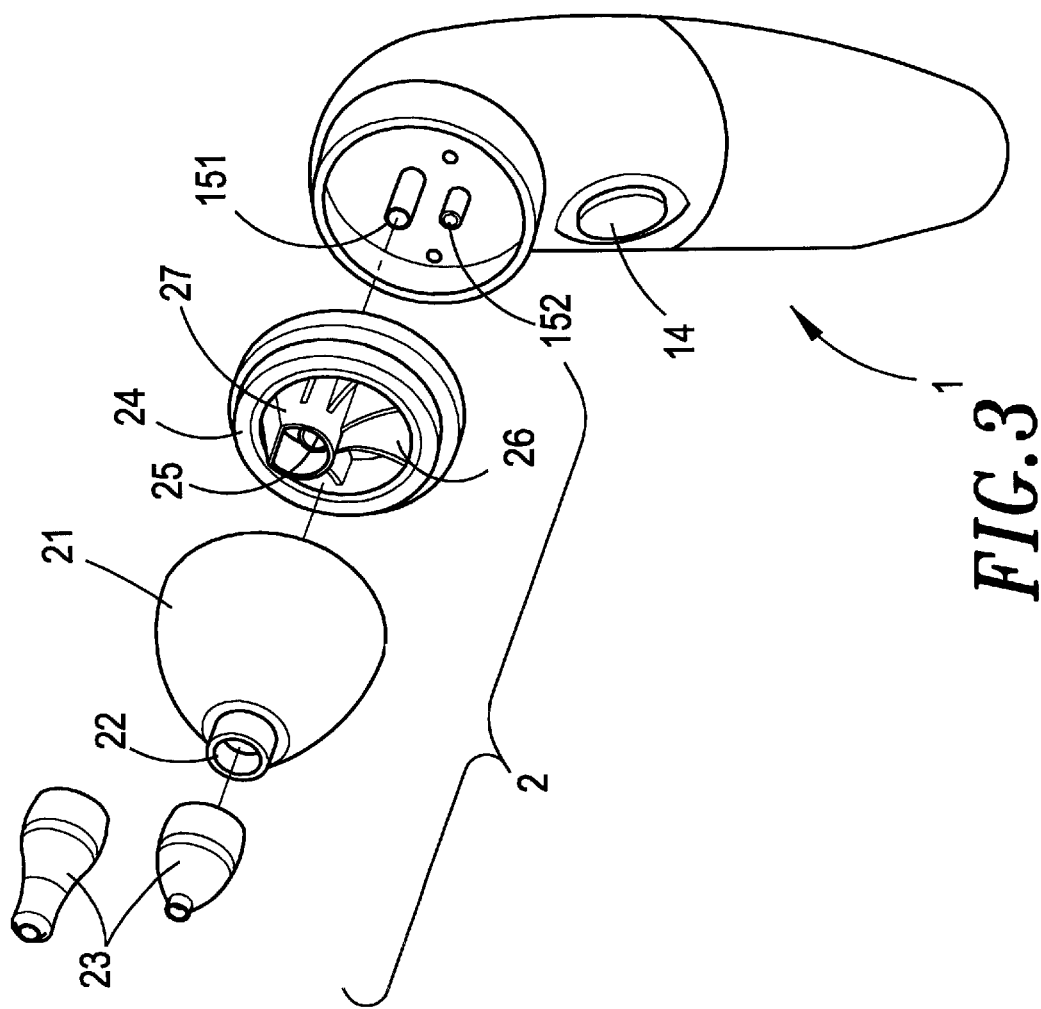
FIG. 3 is a three dimensional exploded view showing component parts of the present invention.

To enable a further understanding as to the basic construction, functions, and innovative features of the present invention, refer to the following detailed description of the invention and the accompanying drawings from FIG.1 through FIG.4. The cleansable multi-purpose nasal discharge aspirator according to the present invention comprises a housing 1, a power supply source (a battery unit) 11, a driving motor 12, a pressure pump 13, a switch 14, a pressure chamber 15, a detachable sucking disc 21, an inhaling tube 22, an air conducting tube 25, and a barrier unit. The power supply source 11 (a battery unit), the driving motor 12 for driving the pressure pump 13 to produce pressurized fluid, are all accommodated in the housing 1, but the switch 14 for controlling motor ON/OFF, is mounted on the outer surface of the housing 1. The pressure chamber 15 provided at the front end of the housing 1 and having an air intake aperture 151 and an air discharge aperture 152 is connected with an open end of the pressure pump 15. The detachable sucking disc 21 is fitted to the air intake aperture 151 from outer side of the housing 1, while the air discharge aperture 152 is communicated with outside of the housing 1. The inhaling tube 22 is connected to the front end of the sucking disc 21, and the air conducting tube 25 is connected to the joint portion of the sucking disc 21 and the air intake aperture 151. The barrier unit is interposed between the inhaling tube 22 and the air conducting tube 25. The barrier unit includes a tubular spacer 27 and a plurality of slanted arcuate baffles 26. The air conducting tube 25 is encompassed by the tubular spacer 27, and the slanted arcuate baffles 26 are radially disposed between the tubular spacer 27 and the inner fringe on the base of the sucking disc 21 such that a pressure is developed through actuating the pressure pump 13 and inhales the nasal discharge into the sucking disc 21 through the inhaling tube 22, the inhaled nasal discharge is detained in the slanted arcuate baffles region by the tubular spacer 27 so that the nasal discharge is kept thereof without infringing into the pressure chamber 15 to contaminate the apparatus. The remaining inhaled air is released from the air discharge aperture 152 by way of the air conducting tube 25 and the air intake aperture 151. The used sucking disc 21 can be detached and sterilized for reuse.

Meanwhile, the housing 1, especially the boundaries of the battery compartment and the switch 14 is made hermetical and water tight such that the air intake aperture 151 is submergible into water to wash the pressure chamber 15 contaminated by occasional infringement of little amount of nasal discharge particles thereinto by means, of driving the motor 12 and introducing clean water into the apparatus.

For understanding the construction, functions, and features for a second embodiment of the present invention, reference should be made to FIGS. 5 and 6, wherein the sucking disc 21 is replaceable by a tool head 3 for imbibing acnes. The tool head 3 has a cap 31 fitted on the housing 1 to the air intake aperture 151 and air discharge aperture 152.

An imbibing nipple 33 is inserted into the air intake aperture 151 through an opening 32 of the cap 31. Two different imbibing heads 331 and 332 are respectively provided at two ends of the nipple 33, either head 331 or 332 is usable for imbibing acnes at the user's free selection.

Figure 8:
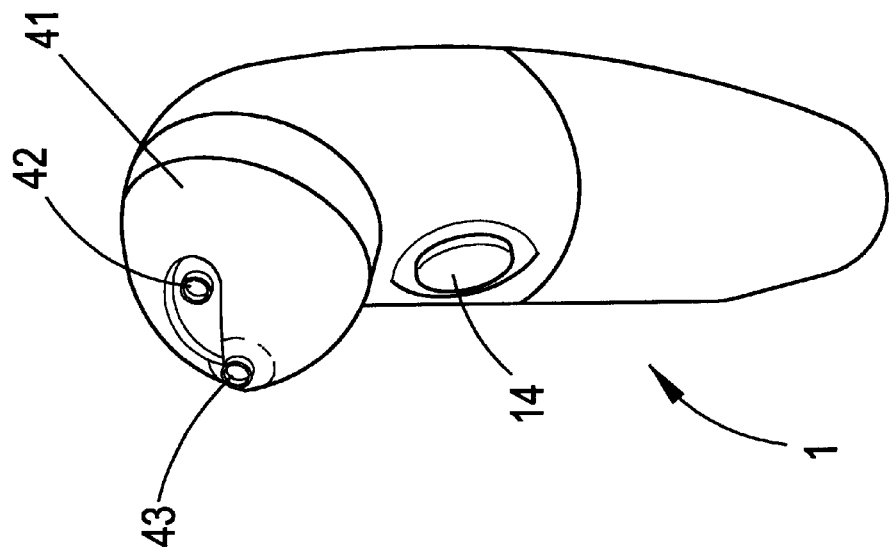
FIG. 8 is a three dimensional view showing the assembled unit in a third embodiment of the present invention.
Figure 7:
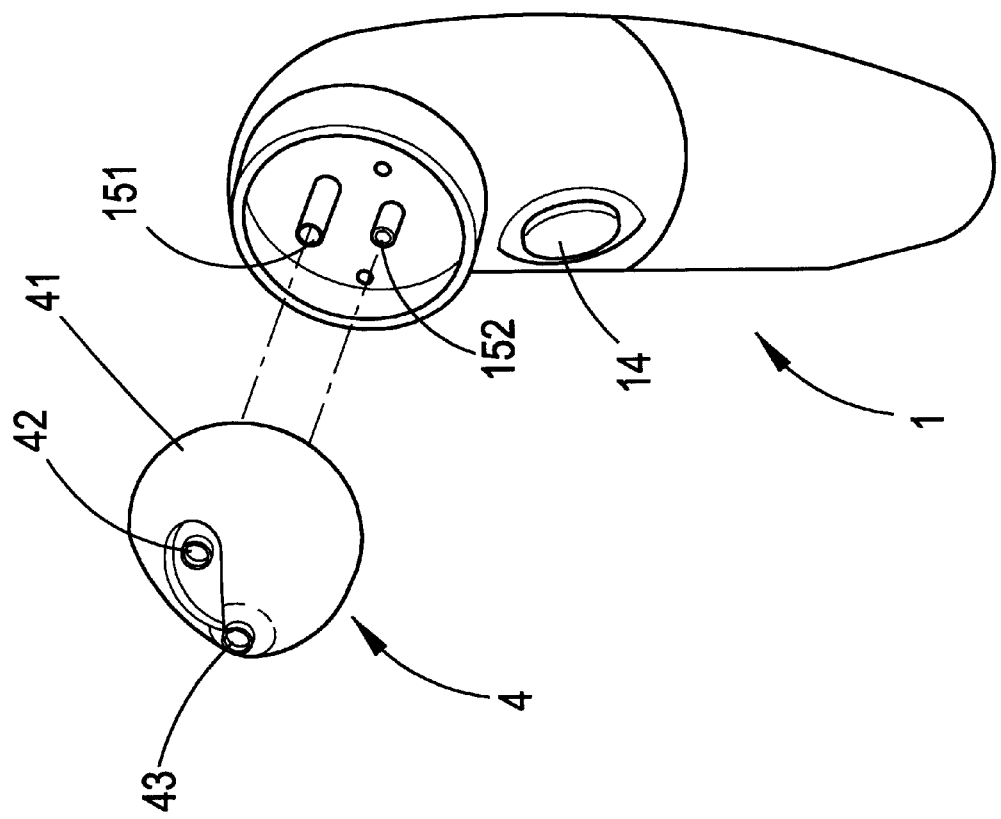
FIG. 7 is an exploded cross sectional view in a third embodiment of the present invention.

For understanding the construction, functions, and feature for a third embodiment of the present invention, reference should be made to FIGS. 7 and 8 wherein the sucking disc 21 is replaceable by a tool head 4 for eyes or nose syringing. The tool head 4 has a cap 41 with a water intake tube 42 and a water ejection tube 43 installed thereon. One end of the water intake tube 42 is connected to the air intake aperture 151, while its other end is connected to an external water supply source (not shown). The water ejection tube 43 is connected to the air discharge aperture 152. With this structure, water introduced from the external water supply source via the water intake tube 42 is ejected from the water ejection tube 43 by repeated suction/ejection operation for performing syringing of nose or eyes.

From the above description, it is noted that the aspirator of the present invention has several noteworthy advantages over any conventional apparatus. Those are:

1. The aspirator of the present invention is equipped with a sucking disc having a nasal discharge barrier unit so as to gather the nasal discharge in a restricted region thereby preventing contamination of inner mechanical components, and the sucking disc is detachable so as to easily discard the dirty content of the aspirator thereby keeping it always clean.
2. The aspirator of the present invention is enclosed with a water tight housing able to withstand submerging in water for cleaning the pressure chamber which is contaminated by occasional infringement of little amount of nasal discharge.
3. The aspirator of the present invention is functionalbe as both sucking and ejection apparatus by adapting variety of working heads so as to perform multi-purpose effect.

A variety of modifications and variations of the present invention are possible in light of the above teachings. It is therefore to be understood that within the scope of the appended claims, the present invention may be practiced otherwise than as specially described hereinabove.

What is claimed is:

1. A cleanable multi-purpose aspirator kit, comprising:
   a housing having a switch mounted on an outer surface thereof;
   a power supply source located in an interior region of said housing;
   a driving motor located in said interior region of said housing and electrically coupled to said power supply source through said switch;
   a pressure pump located in said interior region of said housing, said pressure pump coupled to said driving motor to produce a pressurized fluid;
   a pressure chamber positioned at a front portion of said housing and having an air intake aperture and an air discharge aperture, said pressure chamber being connected to an open end of said pressure pump, said air discharge aperture communicating with an ambient environment external to said housing; and,
   a detachable nozzle removably [mounted] mountable on said housing and when mounted to said housing said nozzle overlaying said air intake aperture, said Application/Control Number: 09/886,017 Page 3 detachable nozzle including (a) an inhaling tube being connected to a front portion of said detachable nozzle, (b) an air conducting tube extending into said detachable nozzle from a joint portion thereof and being in fluid communication with said air intake aperture, and (c) a barrier unit, said barrier unit including a tubular spacer circumscribing said air conducting tube, and a plurality of slanted arcuate baffles radially disposed between said tubular spacer and a base of said detachable nozzle to produce a negative region of pressure when said pressure pump is actuated to draw a gaseous nasal discharge into said detachable nozzle.

2. The cleanable multi-purpose aspirator kit as recited in claim 1, wherein said housing is water tight and submersible for cleaning.

3. The cleanable multi-purpose aspirator kit as recited in claim 1, wherein said detachable nozzle is replaceable by a tool head for aspirating acne, said tool head mounted to said housing having a cap fitted to said housing and overlaying said air intake aperture and said air discharge aperture, said cap having an opening formed therethrough, said head including an imbibing nipple inserted onto said air intake aperture through said opening in said cap, said imbibing nipple having a pair of imbibing heads positioned at opposing end portions of said imbibing nipple for selective use by a user.

4. The cleanable multi-purpose aspirator kit as recited in claim 1, wherein said detachable nozzle is replaceable by a tool head for syringing eyes or a nose, said tool head having a cap with a water intake tube and a water ejection tube respectively extending therethrough, when mounted to said housing said water intake tube having one end connected to said air intake aperture an opposing end adapted for coupling to an external water supply source, said water ejection tube being connected to said air discharge aperture such that water is introduced from an external water supply source and ejected from said water ejection tube by repeated suction and ejection operation of said pressure pump.

* * * * *